United States Patent
Scoon

(10) Patent No.: US 10,166,008 B2
(45) Date of Patent: Jan. 1, 2019

(54) RECTAL CLEANING DEVICE

(71) Applicant: Malcolm Edgar Scoon, Upper Marlboro, MD (US)

(72) Inventor: Malcolm Edgar Scoon, Upper Marlboro, MD (US)

(*) Notice: Subject to any disclaimer, the term of this patent is extended or adjusted under 35 U.S.C. 154(b) by 0 days.

(21) Appl. No.: 14/220,131

(22) Filed: Mar. 19, 2014

(65) Prior Publication Data

US 2014/0317867 A1  Oct. 30, 2014

Related U.S. Application Data

(60) Provisional application No. 61/802,278, filed on Mar. 19, 2013.

(51) Int. Cl.
| | |
|---|---|
| A47K 7/08 | (2006.01) |
| A47L 13/18 | (2006.01) |
| A47L 13/19 | (2006.01) |
| A61B 10/00 | (2006.01) |

(52) U.S. Cl.
CPC .......... *A61B 10/0038* (2013.01); *A47K 7/08* (2013.01); *A47L 13/18* (2013.01); *A47L 13/19* (2013.01); *A61B 2010/0003* (2013.01)

(58) Field of Classification Search
CPC .......... A47K 7/08; A47L 13/18; A47L 13/19
See application file for complete search history.

(56) References Cited

U.S. PATENT DOCUMENTS

| | | | | |
|---|---|---|---|---|
| 2,505,409 | A | * | 4/1950 | Kirchner ............ A47L 13/18 15/227 |
| 2,736,052 | A | * | 2/1956 | Tufarolo ............ A47L 13/18 15/227 |
| 3,638,789 | A | * | 2/1972 | Tuszewski .......... A47K 7/02 15/104.94 |
| 3,866,245 | A | | 2/1975 | Sutherland |
| 4,523,348 | A | * | 6/1985 | Petrie ........................ 15/227 |
| 4,788,733 | A | * | 12/1988 | Lerner .................. 15/104.94 |
| 4,902,283 | A | * | 2/1990 | Rojko et al. ............ 604/290 |
| 4,974,730 | A | * | 12/1990 | Deruysscher ............ 206/581 |
| 5,025,503 | A | | 6/1991 | O'Brien |
| 5,438,708 | A | | 8/1995 | Jacovitz |
| RE35,814 | E | | 6/1998 | Olson |
| 6,516,469 | B1 | | 2/2003 | Schaetzel |
| 6,748,603 | B1 | | 6/2004 | Schmitt et al. |
| 6,748,605 | B1 | | 6/2004 | Brinkmann |
| 7,350,257 | B2 | * | 4/2008 | McKay ............ A47L 13/18 15/104.94 |
| 7,584,519 | B2 | | 9/2009 | Ouellette et al. |

(Continued)

FOREIGN PATENT DOCUMENTS

WO  WO2013102256 A1  7/2013

*Primary Examiner* — Randall Chin
(74) *Attorney, Agent, or Firm* — Hoang Steve Ngo

(57) ABSTRACT

A modified glove includes a glove portion and a wipe portion. The wipe portion is attached to the inner or palm surface of the glove, and comes in wet and dry varieties. The wet variety contains water or mild cleaning agents or some combination thereof, and can be scented or unscented. An embodiment of the modified glove is a single modified glove, while another embodiment is multiple modified gloves, such as three modified gloves in one. One aspect of the modified glove is for cleaning the rectal area of an individual. Another aspect of the modified glove is for cleaning other areas of an individual.

15 Claims, 9 Drawing Sheets

(56) References Cited

U.S. PATENT DOCUMENTS

| | | |
|---|---|---|
| 7,647,667 B2 | 1/2010 | Benjamin |
| 7,681,250 B2 | 3/2010 | Friedstrom |
| 7,725,979 B1* | 6/2010 | Held et al. ................. 15/104.94 |
| 7,845,694 B1 | 12/2010 | Lockwood |
| 2002/0026679 A1* | 3/2002 | Widlund ........................ 15/227 |
| 2003/0120180 A1* | 6/2003 | Kaylor ................. A41D 13/087 |
| | | 600/584 |
| 2004/0103467 A1 | 6/2004 | Schmitt et al. |
| 2004/0244132 A1 | 12/2004 | Ouellette et al. |
| 2007/0134486 A1 | 6/2007 | Bansal et al. |
| 2008/0078046 A1 | 4/2008 | Reed |
| 2008/0172767 A1 | 7/2008 | Friedstrom |
| 2009/0188018 A1 | 7/2009 | Bates |
| 2010/0111763 A1* | 5/2010 | Kahn ................. A61B 5/02042 |
| | | 422/400 |
| 2010/0175215 A1 | 7/2010 | Reed |
| 2010/0218326 A1 | 9/2010 | Yamaguchi |
| 2011/0041276 A1* | 2/2011 | Edwards ................. A47L 13/18 |
| | | 15/227 |
| 2012/0216329 A1 | 8/2012 | Dennis |
| 2014/0123419 A1* | 5/2014 | Kirk ........................... 15/104.94 |

* cited by examiner

RECTAL CLEANING DEVICE

CROSS-REFERENCE TO RELATED APPLICATION

The present application claims the priority benefit of U.S. Provisional Patent Application Ser. No. 61/802,278, filed Mar. 19, 2013, which is incorporated herein by reference in its entirety.

BACKGROUND OF THE INVENTION

Field of the Invention

The present invention relates to a rectal cleaning device and a method associated with the device.

Currently, there are a number of solutions for cleaning the rectal area post defecation (toilet paper alone, toilet paper plus individual wipes, the bidet toilet and bath/shower) but they all have significant drawbacks. Toilet paper alone— insufficient cleaning of rectal area, poor sanitation of wiping hand, toilet paper adherence to rectal area, increased undergarment soilage, increased toilet paper use/costs. Toilet paper plus individual wipes—Same problems as with toilet paper alone but to a slightly lesser degree. In addition, this method has a poor disposal plan (soiled wipes in open trash versus flushing and possibly clogging the plumbing). The Bidet toilet—Improved cleaning of rectal area. Otherwise, still same issues as toilet paper alone. Very expensive to own. Bath/Shower—Best cleaning of the rectal area (including modified glove or triplicate). Additionally, the other toilet paper or toilet paper with wipe issues do not apply. On the down side, there is also increased costs associated with increased water use and increased heating (gas, electric, solar, geothermal, etc.). Overall, very impractical and time-consuming.

The present invention device (in the vast majority of human population) is superior to other known solutions and inventions because: (1) rectal areas are significantly better cleaned than with tissue paper alone or tissue paper plus individual common wipes; (2) there is greatly improved sanitation of the wiping hand; (3) there is reduced toilet paper adherence to rectal area; and (4) there is decreased undergarment soilage. Much of the reduced costs associated with the present invention come from less toilet paper use, less water use, reduced loss of undergarments, and fewer plumbing issues.

It would be desirable to have a device that: (a) cleaned the rectal area significantly better than tissue paper alone or tissue paper plus individual common wipes; (b) greatly improved the sanitation of the wiping hand; (c) reduced toilet paper adherence to rectal area; and (d) decreased undergarment soilage. The modified glove with unique wipe attached of the present invention accomplishes these goals. Furthermore, it would also be desirable to have a device that in saving toilet paper also saved money. Therefore, there currently exists a need in the industry for a device and associated method that accomplishes (a) thru (d) above as well as also save money. The modified glove with unique wipe attached or the triplicate modified glove of the present invention accomplishes these goals.

SUMMARY OF THE INVENTION

The present invention relates to a rectal cleaning device and a method associated with the device. With respect to the device, it is an optimized personal care adjunct for use during toilet stops. The present invention consists of a unique wipe attached to the inside finger portion and/or palmar surface of a glove. The device goes well beyond the simple application of toilet paper or toilet paper plus individual wipes (wet wipes) post defecation. Specifically, this invention allows one to not only have a cleaner rectal area post defecation but also stipulates added bonuses of superior hand sanitation, decreased toilet paper adherence to rectal area, and reduced undergarment soilage as well. The core component of the glove component, portion or part of the invention is nitrile, latex, vinyl or rubber, etc. However, the wipe component, portion or part is composed of fiber such as cotton, synthetic material, or mixture of the two. An exceptional pattern for the wipe surface is terry cloth or terry cloth-like but this is not exclusive of other patterns. With respect to this invention, it should be further noted that the wipe comes in wet and dry varieties. With respect to the associated method, it is suggested that toilet paper still be used in the standard way immediately post defecation. In particular, the vast majority of excrement should be removed (swept away) from the rectal area without the use of common individual wipes. At this point, the modified glove with unique wipe (wet wipe) attached is placed on the dominant hand which is then followed by a wiping motion of the rectal area. The now soiled modified glove with attached unique wipe is removed from the hand by turning the glove inside out in the standard fashion and is appropriately discarded. If the rectal area is still unacceptably soiled, a second modified glove with unique wipe attached can be employed as the first. Additionally, a third modified glove (or more) with unique wipe(s) attached can also be applied as deemed necessary. Lastly, a modified glove with unique wipe attached (dry variety) is recommended for finishing up this optimized cleanup job. Alternatively, there is the triplicate modified glove apparatus (triplicate) that can equally be used. The triplicate consists of three modified gloves with their unique wipes attached. All three are fitted one over the other except the innermost modified glove which is fitted directly on the dominant hand. From the outside inwards, the unique wipes attached are positioned wet-wet-dry. Each modified glove is removed one at a time after successive use and discarded.

DETAILED DESCRIPTION OF THE PREFERRED EMBODIMENTS

Referring to FIGS. 1-10, the present invention is a rectal cleaning device and a kit or tray comprising separate components of the rectal cleaning device.

Figure 1:
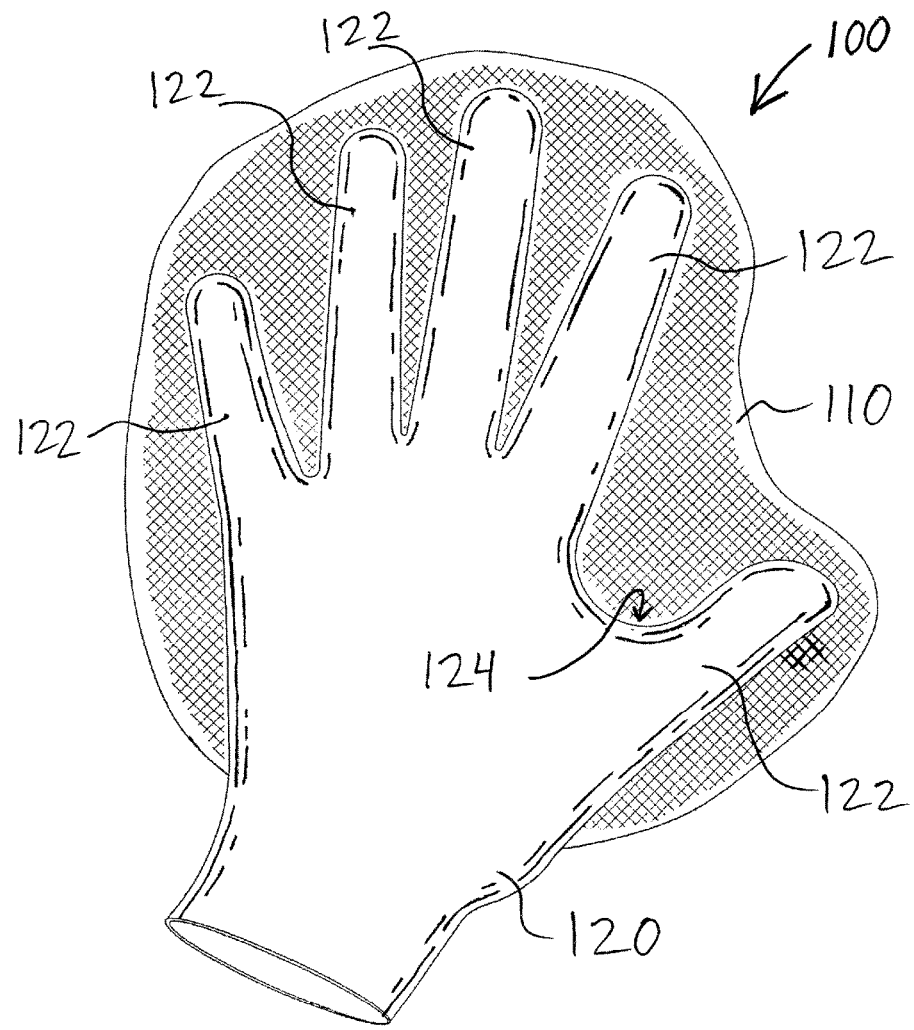
FIG. 1 is a knuckle side, elevational view of an embodiment of a rectal cleaning device (left-handed) according to the present invention, showing a glove component, portion or part attached or secured to a wipe component, portion or part.
Figure 2:
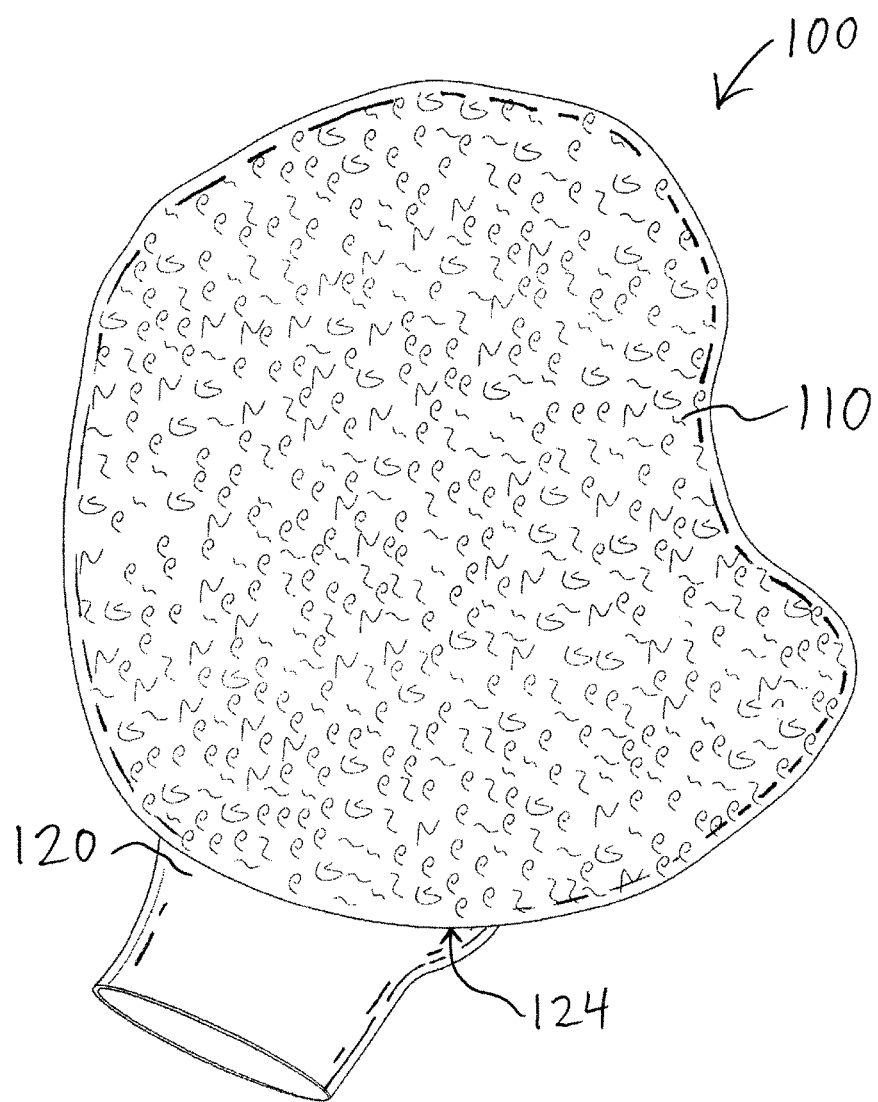
FIG. 2 is a palm side, elevational view of an embodiment of a rectal cleaning device (right-handed) according to the present invention.
Figure 3:
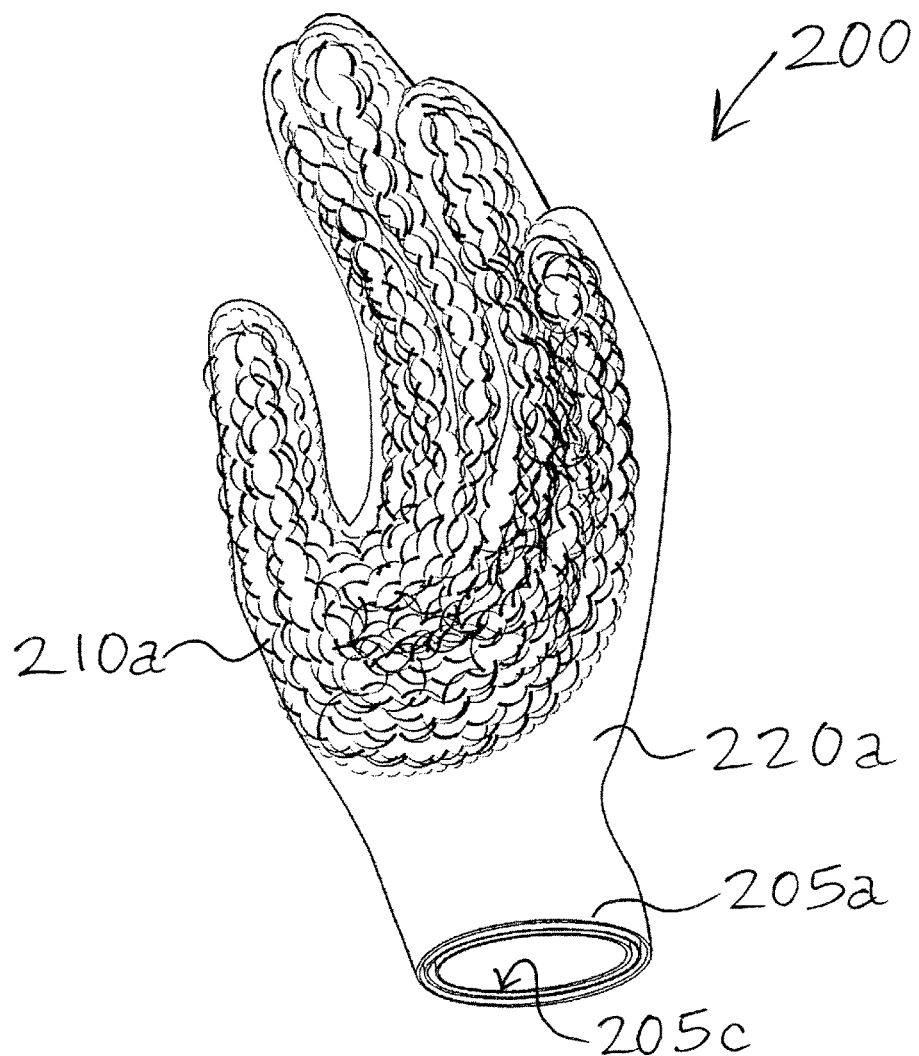
FIG. 3 is a palm side, elevational view of another embodiment of a rectal cleaning device (left-handed) according to the present invention, showing an outermost, modified glove having a wipe component being attached to a palm section and a fingers section of a glove component.
Figure 4:
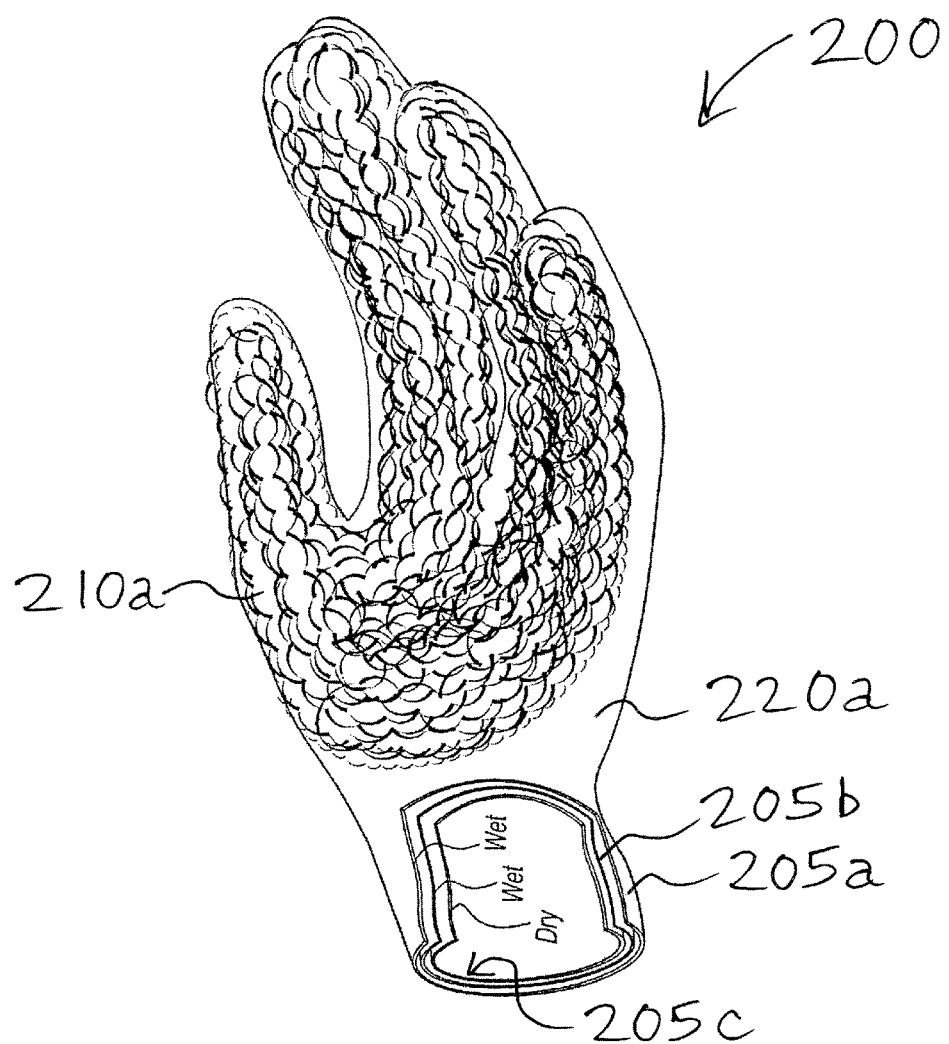
FIG. 4 is a palm side, elevational view of the rectal cleaning device of FIG. 3, showing a cut-a-way view of the outermost, modified glove, an intermediate, modified glove, and an innermost, modified glove.
Figure 5:
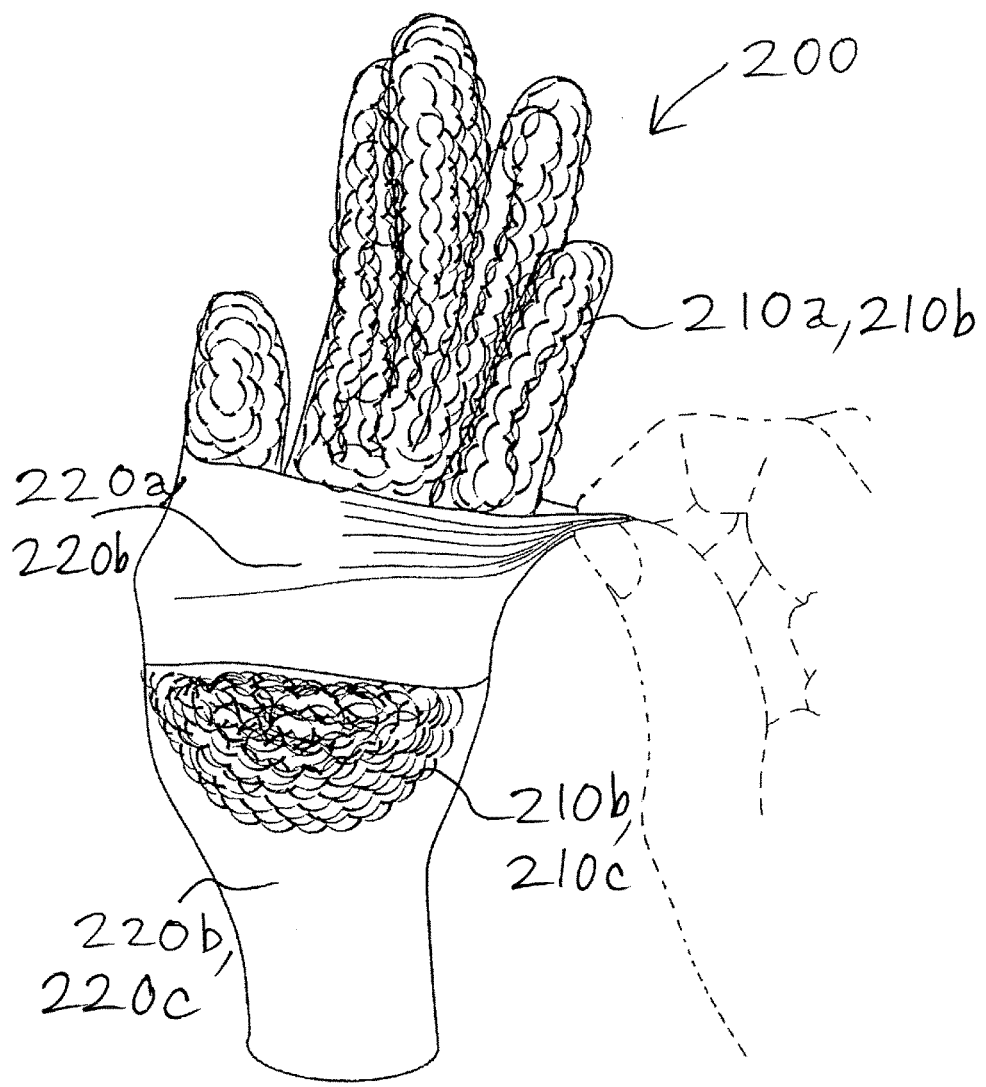
FIG. 5 is a palm side, elevational, environmental view of the rectal cleaning device of FIG. 3, showing the outermost, modified glove being partially removed away from the intermediate, modified glove via an inside-out removal method.

Referring to FIGS. 1-2, the rectal cleaning device is a modified glove 100 with a unique wipe component, portion or part 110 attached to the inside finger portion 122 and/or palmar surface of the glove component, portion or part 120. It is to be used as an adjunct to toilet paper post defecation. The core component of the glove portion 120 of the invention is nitrile, latex, vinyl or rubber, etc.—all of which are impermeable to water. The wipe portion 110 is composed of fiber such as cotton, synthetic materials or a mixture of the two. The wipe portion 110 is terry cloth or terry cloth-like but this is not exclusive of other patterns. Furthermore, the wipe portion 110 comes in wet and dry varieties. The wet variety of the wipe portion 110 contains water or mild cleaning agents or some combination thereof. The attachment between the glove component 120 and unique wipe component 110 is brought about by cementing or gluing or fusing the surfaces together.

The present invention may also have one or more of the following options: The wet variety of the wipe portion 110 of the modified glove 100 can be scented or unscented. Images of detestable things, persons and places, etc. can be embossed on the wet or dry variety of the wipe portion 110 as a comedic or light-hearted feature. In addition to the basic three sizes for the modified glove 100 (large, medium and small), childrens' sizes can also be incorporated. Hospitals and other care facilities can add the use of sterile versions of the modified glove 100 or modified glove apparatus (triplicate glove device) 200. Yet another version of the modified glove 100 and triplicate glove device 200 can be used with babies and infants as the attached unique wipe component 110,210 is reduced in size. Concerning women and menstruation issues, thicker and more absorbent wipe pads 110,210 can be utilized. A more rugged outdoor version (stronger glove and wipe materials) 110,210 is possible for integration into the military as well as the rural and poor areas of the world. Alternate versions of the modified glove 100 and triplicate glove device 200 can also be used to clean wounds (medical personnel for schools and trained staff for professional sports, etc.). Furthermore, there is the cleansing of skin surfaces for a myriad of non-traumatic reasons. For example, the modified glove 100 and triplicate glove device 200 can be used prior to medical procedures like intravenous line placement, blood drawing and spinal tapping, etc. Similarly, the sterile and non-sterile versions of the modified glove 100 and triplicate glove device 200 can also be used in veterinary practice. The application of cosmetics (personally or via a cosmetic artist) would be enhanced with the use of the modified glove 100 or triplicate glove device 200. Then, there is use on the skin surface (cleaning and disinfecting) after a service has been rendered, like shaving, haircuts and nail care, etc.

In its most complete form, the present invention device is made up of the following components: A modified glove 100 with a unique wipe component 110 attached to the inside finger portion 122 of the glove component 120. It is to be used as an adjunct to toilet paper post defecation. The core component of the glove portion 120 of the invention is nitrile, latex, vinyl or rubber etc.—all of which are impermeable to water. The wipe portion 110 is composed of fiber such as cotton, synthetic materials or a mixture of the two. The wipe surface 110 is terry cloth or terry cloth-like but this is not exclusive of other patterns. Furthermore, the wipe portion 110 comes in wet and dry varieties. The wet variety contains water or mild cleaning agents or some combination thereof. The attachment between the glove component 120 and unique wipe component 110 is brought about by cementing or gluing or fusing the surfaces together. With respect to the associated method, it is suggested that toilet paper still be used in the standard way immediately post defecation. In particular, the vast majority of excrement should be removed (swept away) from the rectal area without the use of common individual wipes. At this point, the modified glove 100 with unique wipe (wet wipe) component 110 attached to the glove component 120 is placed on the dominant hand which is then followed by a wiping motion of the rectal area. The now soiled modified glove 100 with the glove component 120 attached to the unique wipe component 110 is removed from the hand by turning the glove 100 inside out in the standard fashion and is appropriately discarded. If the rectal area is still unacceptably soiled, a second modified glove 100 with unique wipe component 110 attached to the glove component 120 can be employed as the first. Additionally, a third modified glove (or more) 100 with unique wipe(s) component 110 attached to the glove component(s) 120 can also be applied as deemed necessary. Lastly, a modified glove 100 with unique wipe component 110 (dry variety) attached to the glove component 120 is recommended for finishing up this optimized cleanup job.

Figures 6, 7:
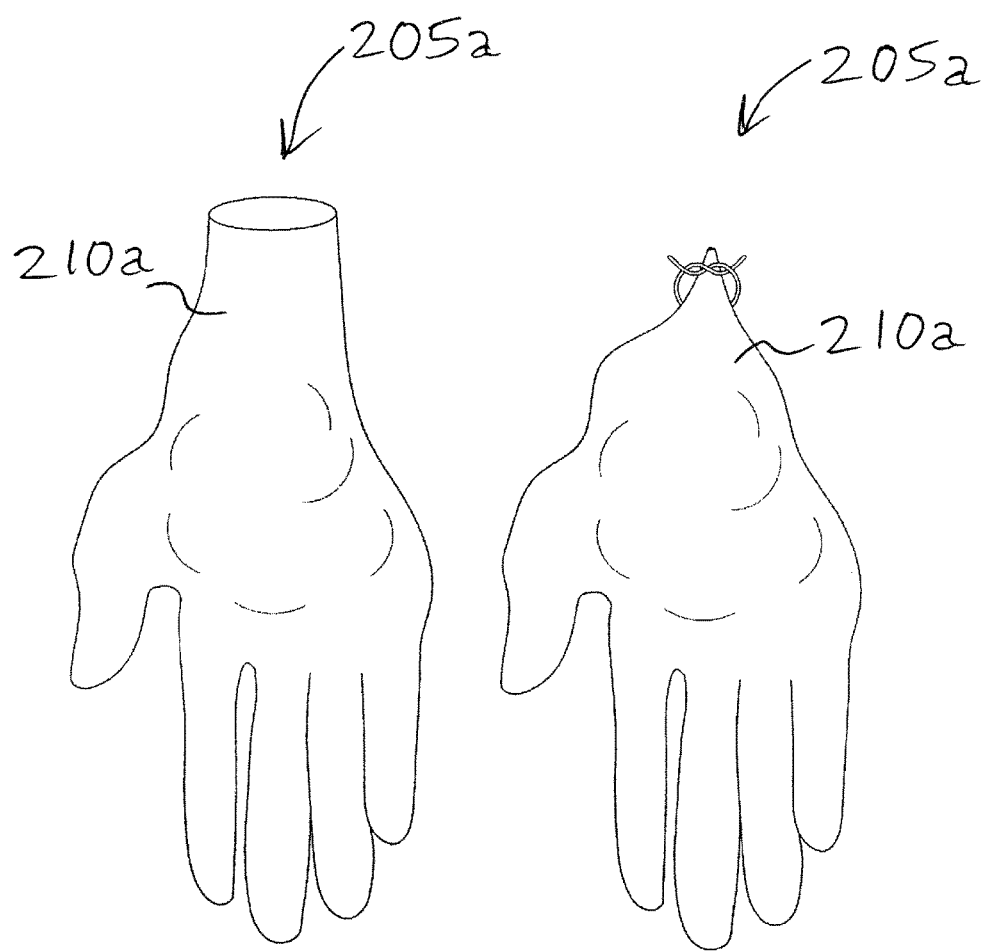
FIG. 6 is a palm side, elevational view of a further embodiment of a rectal cleaning device (right-handed) according to the present invention, showing an outermost, modified glove being totally removed from the rectal cleaning device wherein the outside of the outermost, modified glove now faces inward and the inside of the outermost, modified glove now faces outward; and the outermost, modified glove having an end that is open.
FIG. 7 is a palm side, elevational view of the outermost, modified glove of FIG. 6, showing the outermost, modified glove being totally removed from the rectal cleaning device wherein the outside of the outermost, modified glove now faces inward and the inside of the outermost, modified glove now faces outward; and the outermost, modified glove having an end that is closed by a fastener or tie.

Alternatively, referring to FIGS. 3-7, the rectal cleaning device is a triplicate modified glove apparatus (triplicate glove device) 200 that is equally effective. The triplicate glove device 200 consists of three modified gloves 205*a*, 205*b*,205*c* with their unique wipe components 210*a*,210*b*, 210*c* attached to the glove components 220*a*,220*b*,220*c*—all are fitted one over the other except the innermost, modified glove 205*c*, with its wipe component 210*c* and glove component 220*c*, which is fitted directly on the dominant hand. From the outside inwards, the three modified gloves 205*a*, 205*b*,205*c*, with unique wipe components 210*a*,210*b*,210*c* attached to the glove components 220*a*,220*b*,220*c*, are positioned wet-wet-dry. Each modified glove 205a,205b,205c is removed one at a time after successive use and discarded. As shown in FIG. 7, each modified glove 205a,205b,205c may be tied up with a fastener or tie prior to being discarded.

The present invention is unique in that it is structurally different from other known devices or solutions. More specifically, the present invention is unique due to the presence of a modified glove 100, that is, a glove component 120 with a distinctive wipe component 110 attached to the inner or inside surface 124 of the glove component 120. The present invention includes a triplicate (three modified gloves 205a,205b,205c in one) glove device 200. Both the single modified gloves 100 and the triplicate glove device 200 virtually eliminate the transfer of fecal material to the hands post defecation while greatly improving the cleanliness of the rectal area.

A) The modified glove 100 can in some situations be exchanged for a modified mitt where a unique or distinctive wipe is similarly attached to the inside or inner portion of the mitt. The purpose of the variation could be for occasionally better operation, etc. B) The triplicate or triplicate modified glove device 200 is not exclusive of other multiplier combinations such as the duplicate or the quadruplet. These other multiples can have their own distinct advantages. C) The sequencing combination for the wipes 210a,210b,210c may be different from outside to inside. For example, instead of wet-wet-dry, we may have wet-dry-dry. The choice of one versus the other could be made recognizing the current condition of the fecal material in focus. D) A simple common glove on the non-dominant hand while using the modified glove 100 or triplicate glove device 200 may enhance the overall sanitation level of both hands during the wiping procedure.

Additional Embodiments

Figure 8:
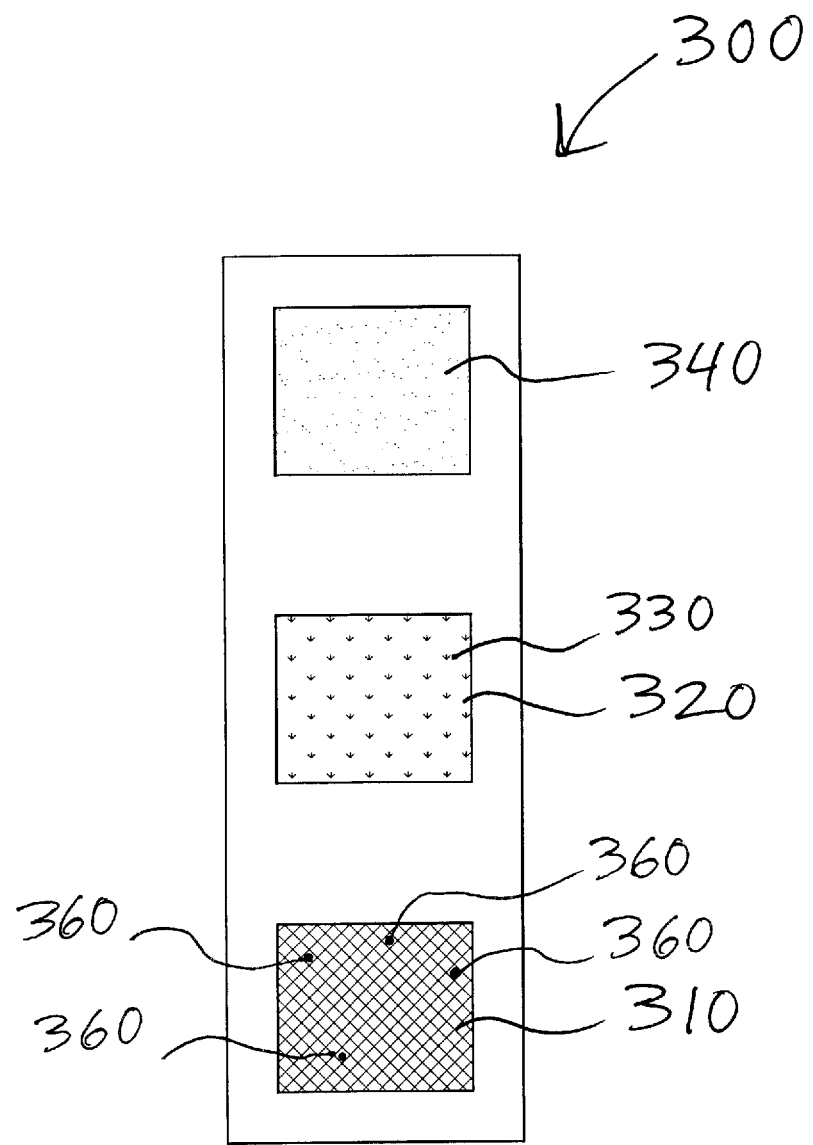
FIG. 8 is a top view of a kit or tray comprising components of a rectal cleaning device according to the present invention, showing a pair of simple gloves, a partially-modified glove component with an attachment or securing component, and a wipe component.
Figure 9:
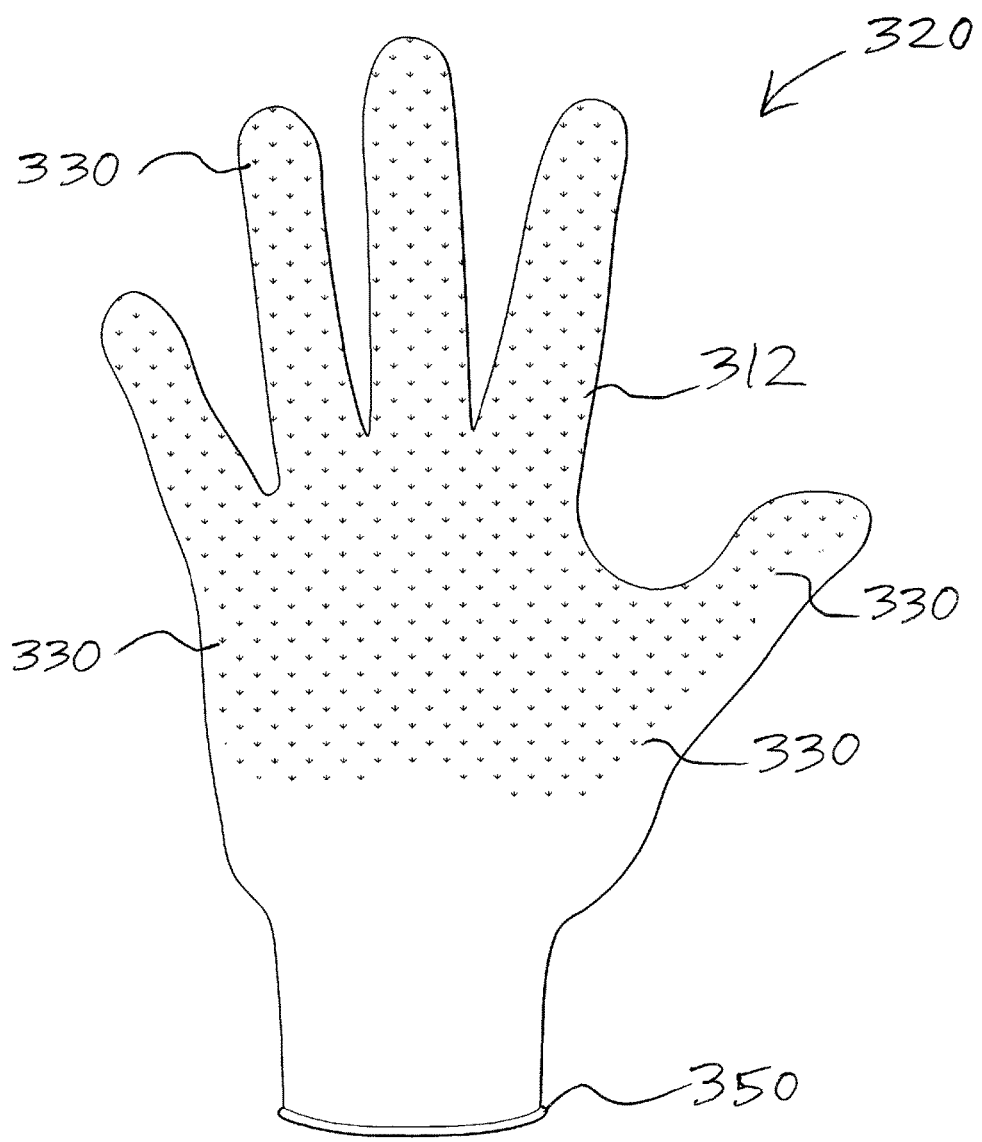
FIG. 9 is a palm side, elevational view of an additional embodiment of a rectal cleaning device (right-handed) according to the present invention.
Figure 10:
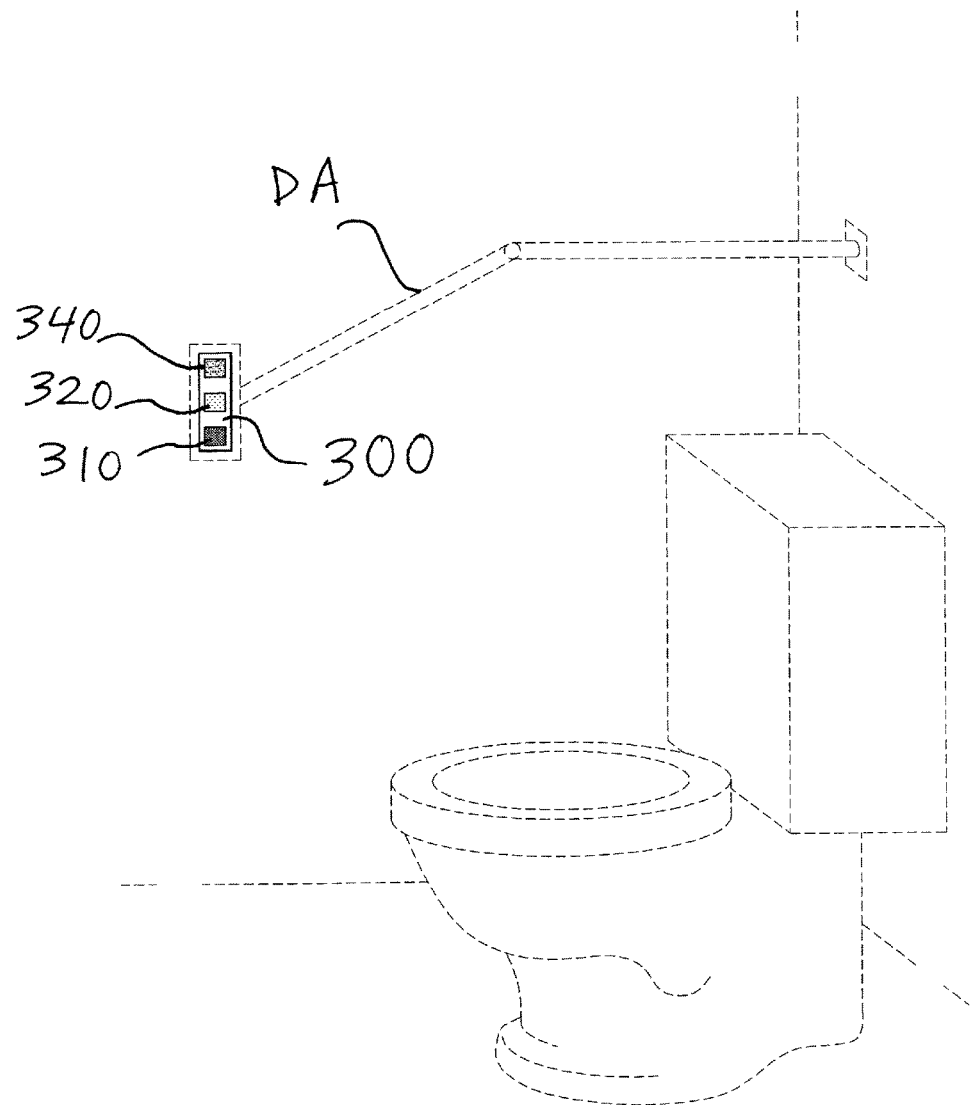
FIG. 10 is a perspective, environmental view of the kit or tray of FIG. 8, showing the kit or tray being mounted, attached or secured in a restroom.

A) Referring to FIGS. 8-10, the rectal cleaning device is a partially-modified glove 320 and unique wipe 310 are not initially attached to one another. The partially-modified glove 320 is different in that the skin of the partially-modified glove 320 is slightly thickened in the palm portion of the wiping hand (covering fingers, palm and thumb). The unique wipe 310 is modified to the extent that it is also slightly or moderately thickened on one of its two large surfaces comparatively speaking. On both of the two inward facing surfaces of the partially-modified glove 320 and the unique wipe 310 would be a Velcro or "Velcro-like" pattern 330. These differences would allow both of these surfaces to adhere to each other at the appropriate time. The unique wipes 310 would come laid out in a tray or kit 300 with some separation if more than one is provided in any given kit or tray 300. The partially-modified glove 320 would be single, double-gloved or triple-gloved. As in the first embodiment, it is suggested that a person first wipe him or herself to best of their ability using a toilet paper and a pair of simple (rubber or vinyl etc.) gloves 340 provided in the kit or tray. Alternatively, the wiping hand would already have a simple glove 340 overlaying the partially-modified glove 320 that can easily be removed after using toilet paper and before attaching one or more unique wipes 310. For example, if a triple partially-modified glove 320 is used, one picks up first a unique wet wipe 310 which immediately adheres to the palmar surface of the partially-modified glove 320. After use, the outer partially-modified glove 320 is pulled off (everted or turned inside out) with the attached wipe 310 and discarded. The same scenario is repeated for the second unique wipe 310 except now the middle partially-modified glove 320 is used for attachment purposes. Lastly, the innermost or third partially-modified glove 320 is used to pick up and attach the last remaining unique dry wipe 310. Upon use, it is also pulled off and discarded with the wipe attached. Universally, either with this embodiment or the first (unique wipes always attached to modified gloves), it has been found useful in the pulling off or eversion process to first "ball up" the wiping hand.

B) Some unique wipes' outer surface 312 would be impregnated with test indicators 360 of stool parameters like occult blood, fat or mucous that would in turn digitally communicate with a specific software application. That application could be downloaded on any smart phone or computer so that almost instant results would be available for the user or if forwarded to the user's doctor.

C) Whether the triplicate glove device 200, doublet or singlet (earlier embodiment) or this embodiment (single, double or triple-glove) each partially-modified glove 320 has a tab or marking on the side indicating "wet", "wet-dry" or "wet-wet-dry," etc. to remind the user.

D) The tray or kit 300 can be placed on the floor next to the toilet, on a nearby stall wall or on a "dentist office-like" attachment DA having a long jointed or unjointed arm that swings out with a hard flat surface (small tabletop) on which the tray or kit 300 can be placed while it's in use. The tray or kit 300 would have on the bottom some sticky gummy substance (not unlike that used to adhere new credit cards to sheet of paper with instructions that is to be mailed). This would allow the tray or kit 300 to remain relatively stationary on the floor, the stall wall or the tabletop. The recommended attachment would be made of metal, plastic any hard non-porous substance or a combination thereof. An alternative support mechanism would be a wall fold-out table not unlike that seen for changing infants and toddlers but somewhat smaller and it would be located adjacent to the toilet.

E) Outer lining of all partially-modified gloves (near the opening for the hand) 320 would have a ring of adhesive 350 exactly like or similar to that described for the bottom of the tray or kit 300. This would facilitate the partially-modified glove 320 staying closed with a twisting motion after removal (turned inside out).

F) Recommend a wall mounted dispenser in every bathroom or stall area for the partially-modified gloves 320—initially attached or unattached embodiment. The scenario is not unlike some dispensers used for sanitary napkins in many "Women(s)" bathrooms.

G) Since one of the main objectives is to keep fecal material (and urine to some degree) off of bathroom users hands immediately post defecation, I propose the creation of small disposable faucet and door knob covers (made of rubber or plastic or some soft impermeable substance). They would be used to help keep one's hands clean after using a partially-modified glove 320, washing with soap and then drying those hands. These special covers would be disposable and found in the tray or kit 300.

What is claimed is:
1. A cleaning glove device comprising:
an outer glove comprising a glove component and a wipe component,
wherein said glove component of said outer glove has a plurality of finger compartments for separately receiving each finger and a thumb of a user,
wherein at least one of said plurality of finger compartments has a corresponding portion of said wipe component of said outer glove secured or attached to at least a palmar finger surface of said finger compartment, and wherein said wipe component of said outer glove may be of a wet variety or dry variety; and at least one inner glove, wherein each of said at least one inner glove is positioned inside said outer glove, wherein each of said at least one inner glove comprises a glove component and a wipe component, wherein said glove component of each of said at least one inner glove has a plurality of finger compartments for separately receiving each finger and a thumb of the user, wherein at least one of said plurality of finger compartments has a corresponding portion of said wipe component of each of said at least one inner glove secured or attached to at least a palmar finger surface of said finger compartment, and wherein said wipe component of each of said at least one inner glove is a dry variety.

2. The cleaning glove device according to claim 1, further comprising an image being embossed on at least one of said wipe components of said outer glove and said at least one inner glove.

3. The cleaning glove device according to claim 1, wherein at least one of said wipe components of said outer glove and said at least one inner glove is manufactured of terry cloth or terry cloth-like material.

4. The cleaning glove device according to claim 1, wherein said outer glove further comprises at least one test indicator of stool parameters.

5. The cleaning glove device according to claim 1, wherein said cleaning glove device is sterile.

6. A cleaning glove device comprising:

a first glove comprising a glove component and a wipe component, wherein said glove component of said first glove has a plurality of finger compartments for separately receiving each finger and a thumb of a user, wherein at least one of said plurality of finger compartments has a corresponding portion of said wipe component of said first glove secured or attached to at least a palmar finger surface of said finger compartment, and wherein said wipe component of said first glove may be of a wet variety or dry variety; and at least one additional glove, wherein each of said at least one additional glove is positioned separately from said first glove, wherein each of said at least one additional glove comprises a glove component and a wipe component, wherein said glove component of each of said at least one additional glove has a plurality of finger compartments for separately receiving each finger and a thumb of the user, wherein at least one of said plurality of finger compartments has a corresponding portion of said wipe component of each of said at least one additional glove secured or attached to at least a palmar finger surface of said finger compartment, and wherein said wipe component of each of said at least one additional glove is a wet variety or a dry variety.

7. The cleaning glove device according to claim 6, further comprising an image being embossed on at least one of said wipe components of said first glove and said at least one additional glove.

8. The cleaning glove device according to claim 6, wherein at least one of said wipe components of said first glove and said at least one additional glove is manufactured of terry cloth or terry cloth-like material.

9. The cleaning glove device according to claim 6, wherein at least one of said first glove and said at least one additional glove further comprises at least one test indicator of stool parameters.

10. The cleaning glove device according to claim 6, wherein said cleaning glove device is sterile.

11. A rectal cleaning device comprising:

an outer glove comprising a first glove component and a first wipe component, wherein said first glove component has a compartment for receiving each finger and a thumb, wherein said first wipe component is secured or attached to at least one of a palmar finger surface and a palmar surface of said first glove component, and wherein said first wipe component may be of a wet variety or dry variety;

a first inner glove comprising a second glove component and a second wipe component, wherein said second glove component has a compartment for receiving each finger and a thumb, wherein said second wipe component is secured or attached to at least one of a palmar finger surface and a palmar surface of said second glove component, and wherein said second wipe component may be of a wet variety or dry variety; and a most inner glove comprising a third glove component and a third wipe component, wherein said third glove component has a compartment for receiving each finger and a thumb, wherein said third wipe component is secured or attached to at least one of a palmar finger surface and a palmar surface of said third glove component, and wherein said third wipe component may be of a wet variety or dry variety.

12. The rectal cleaning device according to claim 11, further comprising an image being embossed on at least one of said wet or dry variety of said first, second and third wipe components.

13. The rectal cleaning device according to claim 11, wherein at least one of said first, second and third wipe components is manufactured of terry cloth or terry cloth-like material.

14. The rectal cleaning device according to claim 11, wherein said outer glove further comprises at least one test indicator of stool parameters.

15. The rectal cleaning device according to claim 11, wherein said rectal cleaning device is sterile.

* * * * *